United States Patent [19]

Deardorff

[11] Patent Number: 4,526,725
[45] Date of Patent: Jul. 2, 1985

[54] CATALYST COMPOSITION AND METHOD FOR THE MANUFACTURE OF ESTERS

[76] Inventor: Don L. Deardorff, 43 Gould Pl., East Greenwich, R.I. 02818

[21] Appl. No.: 482,926

[22] Filed: Apr. 7, 1983

[51] Int. Cl.$^3$ .......... C07F 7/28; C07C 67/08; C07C 67/48
[52] U.S. Cl. ............................................. 556/56; 560/1; 560/99; 560/100; 560/103; 560/127; 560/204; 560/265; 502/167
[58] Field of Search .............. 260/429.5; 560/99, 100, 560/103, 127, 204, 265; 502/167

[56] References Cited

U.S. PATENT DOCUMENTS

| 3,053,883 | 9/1962 | Dean et al. | 560/99 |
| 3,056,817 | 10/1962 | Werber et al. | 560/99 X |
| 3,056,818 | 10/1962 | Werber | 560/99 X |
| 3,245,959 | 4/1966 | Roeser | 560/99 X |
| 3,717,672 | 2/1973 | McGee | 560/204 X |
| 4,007,218 | 2/1977 | Ghanayem et al. | 560/99 |
| 4,284,793 | 8/1981 | Sagara et al. | 560/99 X |

FOREIGN PATENT DOCUMENTS 1246346 9/1971 United Kingdom .

Primary Examiner—Natalie Trousof
Assistant Examiner—Vera C. Clarke
Attorney, Agent, or Firm—Barlow & Barlow, Ltd.

[57] ABSTRACT

An improved method for the manufacture of purified esters is provided. The method comprises reaction of carboxylic acids or anhydrides with alcohols in the presence of certain novel chelated titanate catalysts having unique structural features that provide means for simplification of the refining process as well as for improving reaction rates, ester yield and product quality.

8 Claims, No Drawings

CATALYST COMPOSITION AND METHOD FOR THE MANUFACTURE OF ESTERS

BACKGROUND OF THE INVENTION

Esters that are derived from carboxylic acids and aliphatic alcohols and which are manufactured as residue products comprise an important and broadly used class of compounds. This invention relates to an improved method for manufacture of those compounds.

Commercial methods for manufacture of residue product esters generally use a catalyst to improve the rate of reaction and the degree of conversion of acids to ester. In most instances these catalysts must be removed from the crude ester product so that it may be refined to give a good quality ester for use in applications requiring high purity. Sulfuric acid is the most widely used catalyst for ester manufacture. It is fast and inexpensive, but has disadvantages of yield and quality, and must be neutralized with caustic and washed from the crude ester. Elimination of washing steps and providing generally more convenient methods of refining, as well as fast reaction rates, higher yields and better quality are highly desirable objectives in the esterification industry and are the concern of much investigation and patent art.

The Werber et al patent, U.S. Pat. No. 3,056,818 of 1962 disclosed the use of organotitanates as catalysts to give high yields, fast rates and good quality esters. This specification also states that the esters need not be washed and that the titanium catalysts need not be removed from the residue product esters. These catalysts, as for example, tetraisopropyl titanate and tetrabutyl titanate, although requiring higher temperatures than the traditional acid catalysts, do provide advantages of a very high conversion rate of acids to ester, while minimizing side reactions which cause color buildup in products and deterioration in the excess alcohols that may be recovered and recycled. It is clear, however, that the titanium catalyst residues, like acid catalyst residues, must be removed from the crude products. Chilton (U.S. Pat. No. 3,818,071), McGee (U.S. Pat. No. 3,717,672), Ghanayem (U.S. Pat. No. 4,007,218), and Sagara (U.S. Pat. No. 4,284,793) among others have pointed to the problems associated with the titanium residues and have disclosed methods to deal with the problems.

The method conventionally used to remove the titanium residues is the same as with acids; that is, washing with aqueous caustic. Most of the other methods proposed also involve treatments with strongly basic materials such as lime (see McGee) or solid alkali (see Sagara), although investigators since Werber have looked for more convenient methods.

An object of this invention is to provide a method for manufacture of esters that does not require caustic wash or separate treatment with strongly basic materials.

The most convenient method for removing the titanium has long been thought to be simple hydrolysis with steam to yield titanium oxides that would be insoluble and removed by filtration. Since the conventional method for removing excess alcohol from an esterification reaction mixture is by steam distillation, the hydrolysis and removal of alcohol could be done at the same time and the process would be simplified to reaction, stripping and filtration.

It is an object of this invention to provide a method wherein refining of the crude ester mixture may be accomplished by steam distillation and subsequent removal of hydrolyzed catalyst, thereby by reducing the process to its simplest form of reaction, stripping and filtration.

Previously it was not practical to refine titanium catalyzed esters in this manner, as the hydrolysis of the titanium catalyst residues during steam distillation varied markedly from ester to ester, and in all cases was incomplete. The consequences of slow and incomplete hydrolysis of the residual titanate catalyst often are severe and include an increase in acid number, retention of color, poor filtration and continued precipitation of titanium insolubles in storage, as well as poor thermal stability and poor electricals.

The reason for this incomplete hydrolysis of the titanium is not clear. Simple tetra-alkyl titanates, as initially added to the reaction mixture, are quite reactive with water and easily hydrolized to insoluble oxides upon treatment with steam at these elevated temperatures. It is likely that the catalyst residues are not the same structures added in the beginning of the reaction, but are larger, more complicated species, less active as catalysts and less easily hydrolyzed. Since the titanates are tetrafunctional and have the added capability of forming coordination complexes to give an effective valence of six, and since they are reactive not only with alcohols and water, but with carboxylic acids, it is not difficult to envision the formation of relatively complex and hindered species, especially in those instances where the acid component of the system is multifunctional. This might explain not only the difficulty in hydrolyzing all of the titanium in the residue products, but also the vastly differing rate and degree of hydrolysis from one instance to another.

It is the object of this invention to provide an improved method for manufacture of esters wherein the process is simplified to the three steps of refining, stripping and filtration.

DETAILED DESCRIPTION OF THE INVENTION

This invention relates to a novel catalyst composition and to an improved method for manufacture of esters. Specifically, this invention relates to a novel concept in esterification catalyst design that provides advantages in rates of reaction, product quality and efficiency of refining procedures. Catalysts suitable to and described in this invention are highly active and versatile catalysts for esterification, being generally more efficient, on a contained titanium basis, than tetraisopropyl or tetrabutyl titanates especially in the later stages of esterification. In the same way, they are shown to be superior to the fully chelated titanates, as for example, triethanolamine titanate (Tyzor TE, duPont), being more active in both ester catalysis and in reactivity toward water than the fully chelated derivatives.

Thus it is an essential feature of this invention that the composition of the catalyst described herein consist of titanium atoms bonded to residues of alkyl alcohol as well as residues of dialkanolamines.

Catalysts that are suitable to this invention are certain alkyl titanium chelates (ATC) whose composition corresponds to

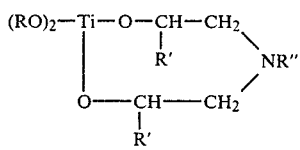

structure I where R is alkyl having 4 to 18 carbon atoms, R' is hydrogen or an alkyl of 1 to 4 carbon atoms, and R" is hydrogen or alkyl of 1 to 10 carbon atoms or alkyl of 1 to 10 carbon atoms or aromatic.

Catalysts represented by structural formula (I), which can be utilized in the present invention, are complex in structure. These catalyst may be prepared by reacting tetraisopropyl titanate with an alcohol containing at least four carbon atoms, and with a suitable poly-(alkanol)amine, in a manner that two of the isopropyl groups are replaced by the higher alcohol and two groups are replaced by the poly(alkanol)amine, thereby forming a cyclic structure with the titanium atom. The residue product contains two alkyl alcohol residue per titanium atom, and one chelating nitrogen atom per titanium atom.

Alkyl groups that are suitable to the invention are primary alcohols with carbon numbers of 4 to 18, with the preferred group being those having 6 to 13 carbon atoms and branching in the two position of the carbon chain. Poly(alkanol)amines suitable to the invention are exemplified by diethanolamine, di-isopropanolamine, N-methyl(diethanol)amine, N-butyl(diethanol)amine and the like.

In a preferred manner for preparing catalysts of this invention, one mol equivalent of tetraisopropyl titanate is treated with one mol equivalent of the appropriate poly(alkanol)amine followed by addition of about 2 to 3 mol equivalents of a suitable alkyl alcohol. The mixture is heated under vacuum in a manner to remove essentially 4 mol equivalents of isopropyl alcohol as it is formed, maximum conditions being on the order of 150° C. and 200 torr. Resultant products are viscous liquids, soluble in oxygenated solvents and aromatics, and slowly reactive with water.

In a typical application of the catalysts and the method described in this invention, carboxylic acids or anhydrides are contacted at elevated temperatures with an excess of alcohol and in the presence of a catalytically effective amount of the catalyst in a manner to remove water as it is formed and until the conversion of acids to ester is essentially complete or the acid number is within prescribed limits. A catalytically effective amount is herein defined an an amount which enables the reactants which are catalyzed to react to the extent greater than if the catalyst was not present. Reactions preferably are conducted at temperatures ranging from 150° C. to 250° C. When esterification is complete excess alcohol is removed by vacuum and steam distillation, which also serves to hydrolyze the catalyst. The product is then filtered to yield high quality ester.

Improvements provided by the use of this method of the present invention, which are illustrated by the examples included herein are (1) increased rates of conversion of acid to ester, compared with conventional tetraalkyl titanates or other metallic catalyst compounds, (2) convenient and efficient hydrolysis of the titanium catalyst residues accomplished during steam distillation of alcohol from the crude ester, (3) stability with increase in acid number during steam distillation, (4) improved filtration characteristics, (5) improved quality of recovered ester with respect to color, heat stability and other properties related to residual impurities, (6) very high yields of products made possible by the elimination of washing.

The improvements in esterification provided by this invention are the result of certain structural features that are specified for the catalysts described herein. It is essential to the concept and to the performance of this invention that the structure of the catalysts molecule contain both alkoxy and certain poly(alkanol)amine chelate structures. Thus, Tyzor TE, which is derived from a reaction of tetraisopropyl titanate with triethanolamine, and which contains no alkyl groups higher than propyl, is an active catalyst for esterification, but does not efficiently hydrolyze during steam distillation and produces a product ester which has high color and an acid number that is significantly increased during steam distillation. In the same way, tetraisopropyl titanate, or other tetra alkyl titanates as, for example tetrabutyl or tetradecyl titanate may be shown, by comparison with chelated catalysts of this invention, to be deficient with respect to both catalytic activity and the ability to produce crude products that may be refined to high quality products by simple steam distillation and filtration procedures.

Preparation of the catalysts compounds of this invention, the method of their use and the advantages provided, in comparison with conventional titanate catalysts and methods, are shown in examples included below. Catalysts of the invention, as for example the compound designated ATC-I, which is a preferred form of the invention and which is prepared from reaction of tetraisopropyl titanate with diethanolamine and with isodecyl alcohol, provide advantages both of catalytic activity and, particularly, in refining of crude products. Thus the compound ATC-I, which contains 10.3 percent titanium, compares favorably in catalytic activity even on a weight basis with both tetrabutyl titanate, which contains 14.1 percent titanium, or with tetra-isopropyl titanate which contains 16.9 percent titanium. This surprising activity, noted especially in the later stages of reaction, provides increased utility of titanium catalysts at low temperatures, even below 170° C. where normally only acid catalysts are of practical use. In the same way, comparison of catalysts of this invention with tetraalkyl titanates demonstrates the utility and improvements in refining simplicity and product quality. While these improvements are to be expected in all ester types where titanates are useful as catalysts, the method is especially advantageous in certain ester types such as trimellitates where color or acid number increase during steam distillation are particular problems.

PREPARATION OF ATC-I CATALYST

A 1-liter, 3-neck flask fitted with thermometer, nitrogen inlet tube and vacuum distillation system was charged with 284 g of tetraisopropyl titanate, 105 g of diethanolamine and 316 g of isodecyl alcohol. The reaction was mildly exothermic, reaching 58° C. Heat was applied along with vacuum to remove 238 g of isopropyl alcohol at final conditions of 140° C. and 100 torr, leaving 466 g of a yellow, slightly viscous liquid residue product designated (ATC-I).

COMPARATIVE EXAMPLE A

A standard esterification apparatus, consisting of a 2-liter 3-neck flask fitted with thermometer, nitrogen inlet tube and Dean-Stark water separator topped with a total reflux condenser, was charged with 296 g of phthalic anhydride, 624 g of 2-ethylhexyl alcohol and 0.5 g of tetraisopropyl titanate catalyst. The mixture was heated strongly and water of esterification started to form at 165° C. Reflux was continued at 210° C. reaction temperature removing water of reaction essentially as fast as it was formed. After 2.5 hours 36 ml of water was collected and the acid number of the ester product was 0.05 mg KOH/g. Excess alcohol was removed by increasing the vacuum to 100 torr as the temperature was allowed to drop to 190° C. Cooling to 150° C., the remaining alcohol was removed by steam distillation at 100 torr using 50 ml of water during 30 minutes. After drying under the same temperature and pressure conditions for 15 minutes, the residue was cooled to 90° C. and filtered through a No. 1 Whatman paper coated with diatomaceous earth. Filtration was difficult, quickly blinding the paper and giving a hazy filtrate with an acid number of 0.14 mg KOH/g and estimated color of 20 APHA.

EXAMPLE I

A reaction was conducted as in Comparative Example A except that 0.5 g of ATC-I catalyst was used and was added to the reaction as the temperature reached 200° C. After 2.5 hours all water of reaction was received and the acid number of the crude product was 0.06 mg KOH/g. Excess alcohol was removed with vacuum and the product was steam distilled at 150° C. and 100 torr using 50 ml of water in 30 minutes. The residue product was cooled to 90° C. and filtered easily and rapidly through a No. 1 Whatman paper yielding a clear di-2-ethylhexyl phthalate ester (DEHP) ($n_D^{25}=1.4851$) with color less than 10 APHA and acid number of 0.03 mg KOH/g.

COMPARATIVE EXAMPLE B

A reaction was conducted as in Example I except that the catalyst employed was 0.5 g of Tyzor TE (triethanolamine titanate, duPont). After 2.25 hours reaction at 210° C., the acid number was 0.06 mg KOH/g, at which time excess alcohol was removed and the product steam distilled with 50 ml water at 150° C. and 100 torr during 30 minutes, leaving a cloudy residue product that was difficult to filter. This hazy DEHP product was measured to have a color greater than 30 APHA and an acid number of 0.36 mg KOH/g.

COMPARATIVE EXAMPLE C

A reaction was conducted as in Example I except that the catalyst employed was 0.5 g of tetraisodecyl titanate (TITD). After 3.25 hours reaction at 210° C. the acid number was 0.02 mg KOH/g at which time excess alcohol was removed and the product steam distilled with 50 ml water at 150° C. and 100 torr during 30 minutes, leaving a cloudy product that was slow in filtration, quickly plugging a No. 1 Whatman paper. The ester filtrate was 15-20 APHA color and had acid number of 0.18 mg KOH/g.

TABLE I

| COMPARISON OF CATALYSTS IN PREPARATION OF TOTM.* | | | | |
|---|---|---|---|---|
| Example | 3(a) | 3(b) | D | 2 |
| Catalyst | ATC-1 | TBT | TBT | ATC-1 |
| Wt. % | 0.25 | 0.25 | 0.3 | 0.3 |
| Rx. Time, min. | 70 | 65 | 120 | 105 |
| Crude AN | 0.1 | 0.1 | 0.05 | 0.04 |
| Final AN | 0.04 | 0.15 | 0.16 | 0.04 |

TABLE I-continued

| COMPARISON OF CATALYSTS IN PREPARATION OF TOTM.* | | | | |
|---|---|---|---|---|
| Example | 3(a) | 3(b) | D | 2 |
| Final color, APHA | 60 | 125 | 150 | 100 |

*Reaction at 220° C. using 20% excess alcohol, and adding catalyst after removing 65% of water.

COMPARTIVE EXAMPLE D

A standard 1-liter esterification apparatus was charged with 144 g of trimellitic anhydride, 351 g of 2-ethylhexyl alcohol and 0.5 g of tetrabutyl titanate. The system was heated to reflux and the kettle temperature maintained at 220° C. by adjusting the pressure. At the end of 2 hours removal of water was complete and the acid number of 0.05 mg KOH/g. The mixture was cooled to 100° C., washed with 50 ml of 1 percent KOH and 3 times with 50ml portions of tap water. The residue was vacuum dried to 200° C. and 50 torr and the remaining alcohol removed by steam distillation using 50 ml of water at 160° C. and 100 torr. The residue was mixed with 0.1 percent of activated carbon for 15 minutes at 110° C. and filtered through a paper coated with filter aid. The TOTM (trioctyltrimellitate) product ($n_D^{25}=1.4825$) was clear with a color of 150 APHA and acid number of 0.16 mg KOH/g.

EXAMPLE II

The reaction of Comparative Example D was repeated except that 0.5 g of ATC-I was used as catalyst. Removal of water was complete and the acid number was 0.04 at the end of 1.75 hours. Heating was discontinued and excess alcohol was removed by reducing the pressure to 50 torr. Remaining alcohol was removed and the titanate catalyst residues hydrolyzed by steam distillation using 50 ml of water during 30 minutes at 150° C. and 100 torr. The residue was cooled to 110° C., mixed with 0.1 percent activated carbon for 15 minutes and filtered through a paper coated with filter aid to yield a clear TOTM product ($n_D^{25}=1.4828$) with color of 100 APHA and acid number of 0.04 mg KOH/g.

EXAMPLE III

A standard 2-liter esterification apparatus was charged with 576 g trimellitic anhydride and 1404 g of 2-ethyl hexyl alcohol. The mixture was heated to reflux, removing water as formed. After 90 minutes the kettle temperature was 185° C. and 70 g of water was collected, representing 65 percent of the theoretical total water expected. At this point the reaction was cooled and the partially reacted crude separated into portion as follows:

(3a) A 450 g portion was charged to a 1-liter apparatus along with 0.3 g (0.22 percent based on TMA present) of ATC-I catalyst, and heated to react at 220° C. under reduced pressure. After 70 minutes all of the water of reaction was removed and the acid number was reduced to 0.1 mg KOH/g. Alcohol was subsequently removed by vacuum and steam distillation at 150° C./100 torr using 50 g of water in 30 minutes. The dried product was heated and mixed with 0.1 percent of activated carbon for 10 minutes at 110° C. and filtered through a layer of diatomaceous earth to yield a clear TOTM ($n_D^{25}=1.4828$) product with color of 60 APHA and acid number of 0.04 mg KOH/g.

(3b) The procedure of (a) was repeated alternatively using 0.3 g of tetrabutyl titanate as catalyst. After 65 minutes of reflux all of the water of reaction was removed and the acid number of the residue was 0.1 mg KOH/g. Subsequent alcohol removal, steam distillation and carbon treatment yielded a clear TOTM product ($n_D^{25} = 1.4827$) with a color of 125 APHA and an acid number of 0.15 mg KOH/g.

PREPARATION OF ATC-II CATALYST

A one-liter flask equipped with nitrogen sparge, addition funnel, thermometer and vacuum distillation system was charged with 142 g tetraisopropyl titanate and 66.5 g di-isopropanolamine. After 15 minutes there was added 158 g isodecyl alcohol and the mixture heated to remove isopropyl alcohol formed in the reaction. The pressure was reduced as needed and in 45 minutes there was collected 115 g of distillate. Final conditions were 160° C. and 500 torr leaving 254 g of a viscous yellow liquid residue product designated ATC-II.

EXAMPLE IV

A standard 1-liter esterification system was charged with 111 g of phthalic anhydride, 284 g of isodecyl alcohol and 0.5 g of catalyst ATC-II. The system was heated to reflux and the temperature was maintained at 210° C. at reduced pressure. At the end of 1.25 hours the water of reaction was collected and the acid number of the residue was measured to be 0.03 mg KOH/g. Heating was discontinued and excess alcohol removed as the pressure was reduced to 100 torr. Adjusting the temperature to 150° C., hydrolysis of the catalyst and removal of remaining alcohol was accomplished by steam distillation using 40 ml water during 35 minutes at 150° C. and 100 torr. After drying for 15 minutes at these conditions the cloudy crude product was cooled to 90° C. and filtered through a No. 1 Whatman paper to yield a clear residue product diisodecyl phthalate (DIDP) ($n_D^{25} = 1.4850$) having an acid number of 0.04 mg KOH/g and a color of 15 APHA.

EXAMPLE V

A standard 2-liter esterification apparatus was charged with 292 g adipic acid and 727 g isodecyl alcohol. The mixture was heated to reflux, removing water as formed. After 30 minutes of reflux the temperature was 215° C. and 40 ml of water was collected, at which time 0.9 g of catalyst compound ATC-I was added to the flask. The pressure was reduced as needed to maintain the reflux temperature at 220° C. After an additional 45 minutes the water of reaction was collected and the acid number of the residue was measured to be 0.01 mg KOH/g. Heating was discontinued and excess alcohol removed as the pressure was reduced to 20 torr. The reaction mixture was cooled to 170° C., the catalyst was hydrolyzed and the remaining alcohol removed by steam distillation using 100 ml water during 2 hours at 100 torr. The residue was filtered with a No. 1 Whatman paper coated with diatomaceous earth to yield a clear residue product diisodecyl adipate (DIDA) ($n_D^{25} = 1.4502$) having an acid number of 0.05 mg KOH/g and color of 15 APHA. The product remained clear after storage for six months at ambient temperature.

EXAMPLE VI

A standard 2-liter esterification apparatus was charged with 296 g of phthalic anhydride, 727 g of isodecyl alcohol and 0.6 g of compound ATC-I as catalyst. The system was heated to reflux and the temperature maintained at 220° C. by adjusting the pressure. The water of reaction was removed and the residue was measured to have an acid number of 0.13 mg KOH/g at the end of 2 hours. Heating was discontinued and excess alcohol was removed while reducing the pressure to 50 torr. The temperature was adjusted to 170° C. and the remaining alcohol was removed by steam distillation using 60 ml of water during 30 minutes at 100 torr. Hydrolysis of the titanate catalyst residues was indicated by formation of a heavy white cloud early in the steam distillation. After drying 15 minutes at 170° C. and 100 torr, the residue was cooled to 90° C. and filtered through a No. 1 Whatman paper to yield 572 g of a clear DIDP ($n_D^{25} = 1.4830$) having a color of 10 APHA and an acid number of 0.02 mg KOH/g. Alcohol content of the residue was 0.12 percent as determined by gas chromatography. An additional 6 g of product remained on the walls of the reaction flask and filter funnel. Conversion of acid to filtered ester product is 99.3 percent. The product remained clear during storage at ambient temperatures for three months.

TABLE II

| Comparative Example | 7a | 7b | 7c | 8a | 8b | 8c |
|---|---|---|---|---|---|---|
| Product | DIDP | | | DIDP | | |
| Alcohol/Acid | 1.2 | | | 1.2 | | |
| Reaction Temp. °C. | 220 | | | 167 | | |
| Catalyst[1] | TBT | TIDT | ATC-I | ATC-I | TBT | — |
| Wt. % | 0.2 | 0.3 | 0.3 | 0.3 | 0.3 | — |
| Ti. % | 0.03 | 0.02 | 0.03 | 0.03 | 0.04 | — |
| Reaction Time, min. | 60 | 85 | 60 | 315 | 345 | 360 |
| Final Acid Number (mg KOH/g.) | 0.04 | 0.06 | 0.02 | 0.03 | 0.1 | 8.4 |

[1]Catalyst added after removing 65% of water in master batch.

EXAMPLE VII

To a standard esterification apparatus was charged 444 g of phthalic anhydride and 1565 g of isodecyl alcohol. The mixture was heated to 217° C. during 75 minutes to yield 48 g of water which is 70 percent of the expected water of reaction. At this point the reaction was cooled and split into portions as follows:

(a) A 535 g portion was placed in a 1-liter apparatus along with 0.3 g of tetrabutyl titanate catalyst and heated to reflux at 220° C. After 60 minutes essentially all of the water of reaction was removed and the acid number of the residue was 0.04 mg KOH/g.

(b) The procedure of (a) was repeated except that 0.3 g of tetradecyl titanate was used as catalyst. After 85 minutes the acid number of the residue was determined to be 0.06 mg KOH/g.

(c) The procedure of (a) was repeated except that 0.3 g of ATC-1 was used as catalyst. After 60 minutes the acid number of the residue was determined to be 0.02 mg KOH/g.

EXAMPLE VIII

A master batch was prepared as in Example VII, removing 62 percent of the water of reaction during 65 minutes of reflux to a maximum of 222° C., at which time the dehydrated batch was cooled, divided into three parts which were compared as follows:

(a) A 525 g portion was placed in a 1-liter apparatus along with 0.4 g ATC-I catalyst and heated under standard conditions to 167° C. Toluene was added to maintain reflux at that temperature. After 300 minutes the acid number of the residue was determined to be 0.11 mg KOH/g.

(b) The procedure of (a) was repeated except that 0.4 g of tetrabutyl titanate was used as catalyst. After 360 minutes the acid number of the residue was 0.13 mg KOH/g.

(c) The procedure of (a) was repeated except that no catalyst was used for the reaction. After 360 minutes reflux the acid number of the residue was found to be 8.6 mg KOH/g. Relative rates of the ATC-I and TBT catalyzed reactions of Example 8a and 8b are summarized as follows:

|  | Acid No. mg KOH/g. Example | |
| --- | --- | --- |
| Time, min. | 8a | 8b |
| 170 | 5.7 | — |
| 185 | — | 3.73 |
| 210 | 2.1 | — |
| 240 | 1.0 | 1.8 |
| 270 | 0.4 | — |
| 300 | 0.11 | 0.9 |
| 330 | 0.03 | 0.13 (360 min.) |

I claim:

1. A catalyst composition comprising an organotitanate compound represented by the formula

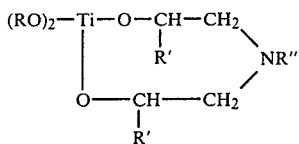

where R is alkyl having four to eighteen carbon atoms, R' is hydrogen or alkyl having one to four carbon atoms and R" is hydrogen or alkyl having one to ten carbon atoms.

2. The catalyst of claim 1 wherein R" and R' are hydrogen.

3. The catalyst of claim 1 wherein R" is hydrogen and R' is methyl.

4. A process for preparing a refined ester which comprises:

(a) reacting one or more mono or di-carboxylic acids or anhydrides or trimellitic anhydrides with excess of aliphatic alcohol in the presence of a catalytically effective amount of an organotitanate catalyst represented by the structural formula:

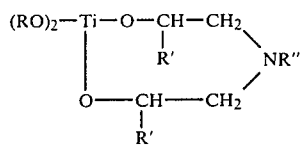

wherein R is alkyl containing from 4 to 18 carbon atoms, R' is hydrogen or alkyl groups having 1 to 4 carbon atoms and R" is hydrogen or alkyl having 1 to 10 carbon atoms, (b) removing the water of esterification until esterification is essentially complete, (c) removing excess aliphatic alcohol and forming insolubles containing catalyst residues by steam distillation, and titanium catalyst residues by filtration.

(d) separating a purified ester product from the resulting titanium catalyst residues by filtration.

5. A process as in claim 4 wherein R is selected from the group of hexyl, isohexyl, iso heptyl, octyl, iso-octyl, 2-3ethyl hexyl, isononyl, isodecyl, decyl, undecyl and iso-tridecyl.

6. A process as in claim 5 wherein R' and R" are hydrogen.

7. A process as in claim 5 wherein R' is methyl and R" is hydrogen.

8. A process as in claim 5 wherein R' is hydrogen and R" is butyl.

* * * * *